(12) United States Patent
Piot et al.

(10) Patent No.: US 7,885,767 B2
(45) Date of Patent: Feb. 8, 2011

(54) METHOD, AN INSTALLATION, AND A COMPUTER PROGRAM FOR ESTIMATING THE INITIAL SIZE OF A POPULATION OF NUCLEIC ACIDS, IN PARTICULAR BY PCR

(75) Inventors: Karine Piot, Montpellier (FR); Pierre Martineau, Saint Gely du Fesc (FR); Claire Lamoure, Viroflay (FR); Franck Molina, Les Matelles (FR)

(73) Assignees: Bio-Rad Pasteur, Marnes-la-Coquette (FR); Centre National de la Recherche Scientifique, Paris Cedex (FR)

( * ) Notice: Subject to any disclaimer, the term of this patent is extended or adjusted under 35 U.S.C. 154(b) by 1260 days.

(21) Appl. No.: 10/998,175

(22) Filed: Nov. 29, 2004

(65) Prior Publication Data
US 2006/0111883 A1   May 25, 2006

(30) Foreign Application Priority Data
Nov. 24, 2004   (FR) .................................. 04 12471

(51) Int. Cl.
*G01N 33/48* (2006.01)
*C12Q 1/68* (2006.01)
*C07H 21/04* (2006.01)
*G06G 7/58* (2006.01)

(52) U.S. Cl. ............................ 702/19; 435/6; 536/23.1; 702/20; 703/11

(58) Field of Classification Search ....................... None
See application file for complete search history.

(56) References Cited

PUBLICATIONS

Rutledge et al, Nucleic Acids Research, 2003, vol. 31, No. 16, pp. 1-6.

*Primary Examiner*—Shubo (Joe) Zhou
(74) *Attorney, Agent, or Firm*—Nixon & Vanderhye P.C.

(57) ABSTRACT

In order to estimate the size of an initial population of nucleic acids in a sample of interest, in particular by PCR, the following steps are performed:
a) providing a model of the effectiveness ($E_n$) of the PCR, the model comprising a constant stage ($E_0$) followed by a non-constant stage, the stages being united by a changeover region having a changeover index ($C_{EEP}$);
b) using the model of effectiveness to express a relationship between the changeover index and a parameter representative of the initial population size; and
c) determining the changeover index by comparison with the experimental measurements, and deducing therefrom the initial population size in the sample of interest.

21 Claims, 5 Drawing Sheets

METHOD, AN INSTALLATION, AND A COMPUTER PROGRAM FOR ESTIMATING THE INITIAL SIZE OF A POPULATION OF NUCLEIC ACIDS, IN PARTICULAR BY PCR

The present invention relates to estimating the initial size of a population of interest in a sample subjected to a succession of amplification reactions.

BACKGROUND OF THE INVENTION

The present invention finds a particularly advantageous, but non-limiting, application in determining an initial quantity of nucleic acids in a sample subjected to a polymerase chain reaction (PCR) in real time. A technique of this type, known as "PCR quantification", is used in particular for evaluating the number of copies of pathogenic agents (e.g. of the human immunodeficiency virus (HIV)) in a sample of body fluids taken from a patient, typically in the context of a medical checkup.

Figure 1:
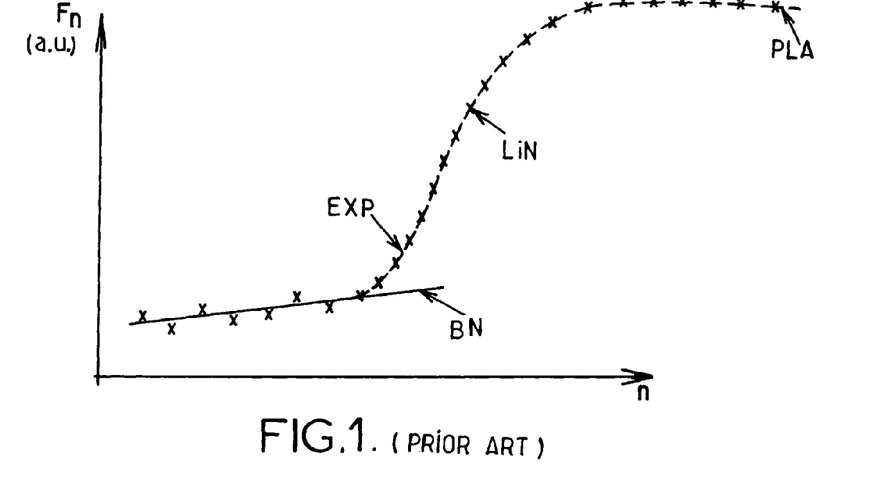
FIG. 1 relates to the prior art and represents variation in the measured quantity of fluorescence as a function of the number of PCR cycles, as described above.

Reference is made to FIG. 1 for a brief description of the diagrammatic appearance of a real time PCR amplification curve with PCR cycle index numbers plotted along the abscissa and, in the example shown, with quantities of fluorescence emitted (in arbitrary units) as measured for each PCR cycle plotted up the ordinate. For each PCR cycle, it should be understood that the sample is subjected to temperature variations enabling DNA polymerase to amplify nucleic acids and enabling the corresponding PCR products to be detected by fluorescent molecules. By plotting the measured fluorescence $F_n$ as a function of PCR cycle number $\underline{n}$, variation is obtained of the type shown in FIG. 1, and comprises at least:

- a first portion BN where fluorescence measurements coincide substantially with the background noise of the apparatus for measuring fluorescence;
- a second portion EXP in which the measured quantities of fluorescence increase in substantially exponential manner;
- a third portion LIN in which the increase in the measured quantities of fluorescence is significantly attenuated and behaves overall in substantially linear manner; and
- a fourth portion PLA in which fluorescence measurements reach a plateau stage.

It should be observed that for the initial PCR cycles (first and second portions), the population of interest increases in substantially exponential manner, whereas for the following cycles (third and fourth portions), other phenomena come into competition with growth in the population of interest, so that said growth is then damped up to the plateau stage PLA.

The document "Mathematics of quantitative kinetic PCR and the application of standard curves" by R. G. Rutledge and C. Côté, published in Nucleic Acids Research, 2003, Vol. 31, No. 16, discloses a method of estimating the unknown initial quantity of nucleic acids in a sample of interest by means of PCR. That method consists in using a plurality of samples having known initial quantities of nucleic acids, referred to as "standards", in order to determine by interpolation the initial quantity of nucleic acids present in the sample of interest.

Figure 2:
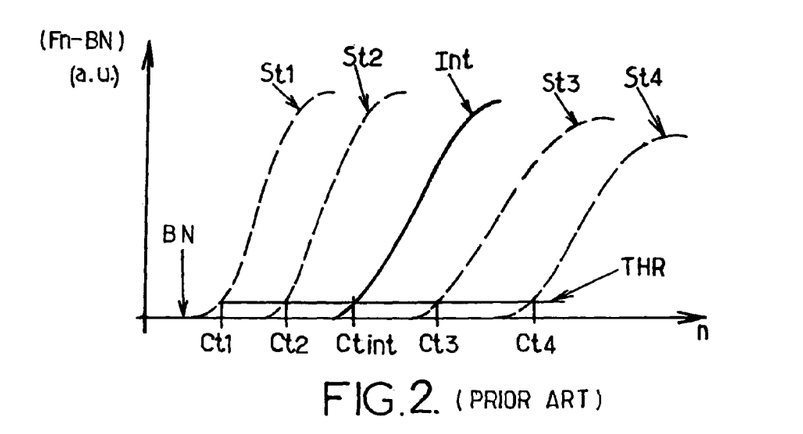
FIG. 2 relates to the prior art and is representative of the increasing quantities of fluorescence that are emitted as a function of the number of PCR cycles, as described above.

In general, the greater the initial quantity of nucleic acids in a sample, the sooner a detectable quantity of PCR product is obtained, i.e. the sooner a detectable quantity of emitted fluorescence is obtained. With reference to FIG. 2, relating to the prior art, it will be understood that the initial population in the standard St1 is greater than that in the standard St2 which is greater than that in the standard St3, etc., since the cycle Ct1 for the standard St1 occurs before the corresponding cycle Ct2 for the standard St2, which occurs before the cycle Ct3 for the standard St3, etc.

Thus, such a Ct cycle, corresponding to the cycle at which the fluorescence measurements reach a fluorescence threshold THR (as shown in FIG. 2), sets at an arbitrary level (typically below the background noise), and acts as a parameter representative of the initial size $N_0$ of a population of nucleic acids subjected to the PCR cycles. Use has been made of this observation in the above-cited prior art to establish a relationship of the kind shown in FIG. 3 between cycle numbers Ct1, Ct2, Ct3, Ct4 for a plurality of standards having known initial populations, and their initial populations $N_0^1$, $N_0^2$, $N_0^3$, $N_0^4$. Thus, by plotting the cycles Ct1, Ct2, Ct3, Ct4, etc. up the ordinates and the logarithm of the initial population sizes $N_0^1$, $N_0^2$, $N_0^3$, $N_0^4$ along the abscissa, a regression slope REG is obtained. On this regression slope PEG, the cycle Ctint detected for the sample of interest is plotted (dashed-line arrow F1). By interpolation on the regression slope REG (dashed-line arrow F2), the initial population size $N_0^{int}$ is then determined for the sample of interest.

Although that method is in widespread use, it nevertheless presents some drawbacks.

Firstly, it requires the use of a plurality of standard samples having respective known initial populations.

Secondly, the method depends on the judgment of the user, since the fluorescence threshold value, as selected by the user, has a direct influence on the values of the Ct cycles in the amplification curves, and consequently on the estimated values for the initial population size in the sample of interest. The threshold value also has an impact on the accuracy of the result, since accuracy is generally better if the threshold is selected to lie in the exponential growth stage EXP of the amplification curve. Nevertheless, in practice, it is difficult for the user to know whether the fluorescence threshold level THR that has been set does indeed correspond to the exponential stage of the curves, and does so for all of the samples (the standard samples and the sample of interest).

Finally, the method assumes without any verification that the population has the same amplification yield in the sample of interest and in all of the standard samples. Thus, if the sample of interest contains PCR inhibitors, as is typically the case, then its result will be falsely lowered.

It should thus be understood that the prior art technique depends on the fluorescence threshold THR as defined by the user. The value selected has an influence on the values of the Ct cycles and consequently on determining the initial quantity in the sample of interest. That is one of the reasons why a large amount of work has recently been undertaken to automate Ct cycle detection and make it reliable.

OBJECTS AND SUMMARY OF THE INVENTION

The present invention seeks to improve the situation by proposing an approach that is completely different.

Firstly, the invention provides a method, the method being implemented by computer means for quantifying in absolute and/or relative manner an initial population of nucleic acids in a sample of interest. The sample is subjected to a succession of applications of a reaction for amplifying the population of interest. In very general manner, this amplification may be undertaken by implementing successive PCR cycles, however any other amplification technique could also be used. Above all, it should be understood that the amplification needs merely to be defined by a reaction yield, as described below. During these successive amplification operations, experimental measurements are taken that are representative of a current population size, at least in the sample of interest. It will be understood that one or more measurements can be taken after or during each amplification reaction without loss of generality.

In a presently preferred definition of the invention, the method in the meaning of the invention comprises the following steps:

a) providing a model of the yield of the amplification reaction as a function of the succession of amplifications, said model comprising:

a substantially constant stage for a first portion of the applications of the amplification reaction; and a non-constant stage for a second portion of the applications of the amplification reaction;

the first and second portions being united by a changeover region in which yield changes over between the constant and non-constant stages, said region having an amplification index corresponding substantially to the changeover;

b) using the yield model to express a relationship involving at least the changeover index and a parameter representative of the initial population size in the sample of interest;

c) determining at least the changeover index by comparison with the experimental measurements; and, in a subsequent or immediately following step d) deducing therefrom the initial population size in the sample of interest.

BRIEF DESCRIPTION OF THE DRAWINGS

Other advantages and characteristics of the invention appear on reading the following detailed description of an implementation given below by way of example with reference to the accompanying figures, in which.

MORE DETAILED DESCRIPTION

Figure 4A:
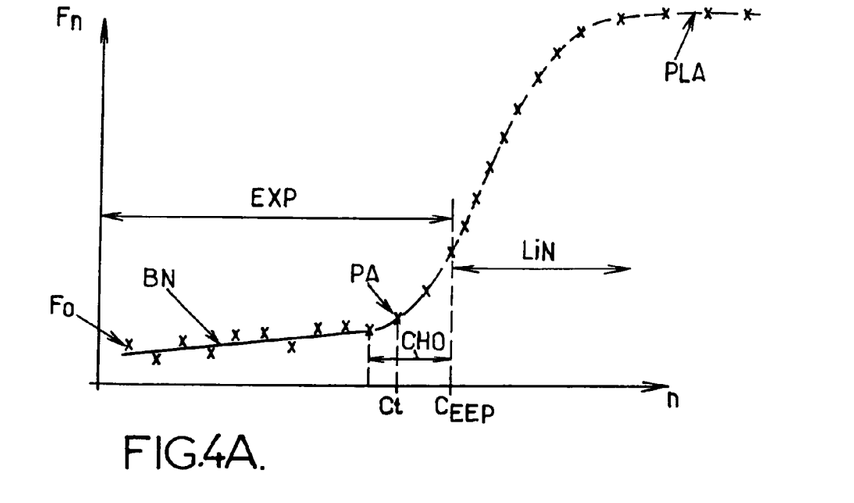
FIG. 4A is a diagram showing variation in the above-described experimental measurements as a function of the succession of amplifications applied to the sample of interest.
Figure 4B:
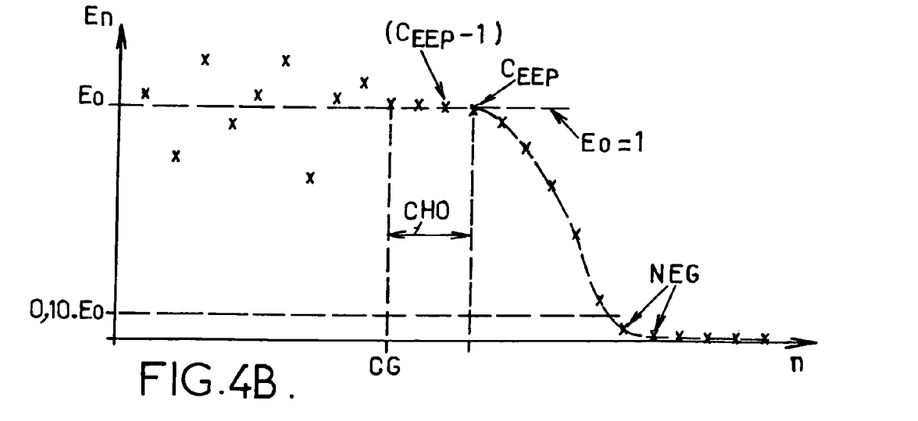
FIG. 4B is a diagram showing variation in the yield of the amplification reaction, obtained from experimental measurements, as a function of the succession of amplifications applied to the sample of interest.

Reference is made to FIGS. 4A and 4B for briefly describing a few principles of the invention illustrating the characteristics of the above method.

Firstly, it should be understood that FIG. 4A plots a succession of experimental measurements $F_n$ representative of the current size of a population of interest which is being subjected progressively to a succession of amplification reactions, each reaction being indexed by an index number $\underline{n}$. In the non-limiting example described herein, this succession of reactions corresponds to a succession of PCR cycles. In this non-limiting example, the experimental measurements $F_n$ correspond to measured quantities of fluorescence on each PCR cycle. Thus, in a quantification method which combines the PCR reaction and the fluorescence emitted by the sample of interest, fluorescent reagents are introduced into the sample so that the fluorescence that is emitted during a PCR cycle is proportional to the size of the nucleic acid population in the sample. Indeed, it can be preferable to perform a plurality of measurements or no measurements at all for certain PCR cycles. Furthermore, more generally, the measurement method may make use of techniques other than fluorescence, even if fluorescence is the method that is often used for quantifying by PCR. Finally, it should be understood that other amplification techniques could be implemented in the context of the present invention, providing it is possible to track variation in the yield of the reaction corresponding to the amplification. Since the example described below relates preferentially to PCR cycles, reference is made to the "effectiveness of the PCR" written $E_n$ for each PCR cycle of index $\underline{n}$, in order to refer to the yield of the amplification reaction.

As mentioned above with reference to FIG. 1, FIG. 4A mainly comprises two regions in which:

during the initial PCR cycles (portion EXP), the population increases substantially exponentially; whereas during the following cycles (the LIN and PLA portions), other phenomena come into competition with growth of the population of interest, so the growth becomes damped.

The following two assumptions are made:

the yield of the reaction $E_n$ is relatively constant during the initial cycles over the portion EXP; and after some number of cycles have been performed, the yield $E_n$ of the reaction starts to decrease over the portions LIN and PLA.

This decrease in yield may have a variety of explanations, in particular a degradation and/or a lack of PCR reagents (DNA polymerase, dNTPs, primers, etc.) and/or inhibition by the products that are made themselves.

It is assumed herein that the yield is initially constant and that it subsequently decreases. Nevertheless, it should be understood that the invention applies more generally to the context of yield:

that is initially constant, which corresponds to a normal situation for growth by amplification; and that is subsequently not constant (decreases or increases) which corresponds to a situation that is substantially abnormal.

In the context of reactions for amplifying the quantity of nucleic acids, it has been found that the yield often changes over from a constant stage to a non-constant stage. In the meaning of the invention, advantage is taken of this observation to deduce therefrom the initial quantity of nucleic acids, as described below in detail. Initially, it is merely stated that the yield can also change over from a non-constant stage during early cycles to a subsequent constant stage. The present invention is equally applicable to such a circumstance. In general, it should therefore be understood that in the meaning of the invention, a changeover of yield between a constant stage and a non-constant stage is detected.

The objective is to find the initial size of the population that has been subjected to amplification. With reference to FIG. 4, it will be understood that the measurement $F_0$ representative of this initial population size, which coincides in practice with the measurement background noise BN, cannot be used on its own for determining directly the initial population size. In the prior art, attempts have been made to quantify this initial population size by making use of the exponential stage, i.e. a stage that occurs typically on exiting background noise. A threshold cycle Ct is then determined (corresponding to point PA for "prior art") in FIG. 4A. As mentioned above, in this region measurements are often affected by noise and it is difficult to determine accurately a threshold cycle Ct representative of exiting background noise.

In a completely different approach, the present invention instead makes use of nearly all of the points of the amplification curve in order to determine accurately a region CHO where the yield changes over between a constant stage and a non-constant stage, typically in present circumstances between the exponential stage EXP and the linear stage LIN. It will be understood that measurements are logically less affected by noise in this region CHO than in the background noise exit region since the region CHO occurs during later cycles. Furthermore, particularly because of the mathematical properties associated with yield, it is shown below that, most advantageously, the number of standards that need to be used for quantifying the initial size of the population of interest is smaller than the number of standards used in prior art quantification.

The relationship for associating the changeover region CHO with the initial size of the population of interest is briefly described below. The yield of an amplification reaction is given by:

$$N_{n+1} = N_n + E_n \times N_n$$

in which:
N$_n$ is the size of the population of interest after an amplification of index $\underline{n}$ in a succession of amplifications;
$N_{n+1}$ is the size of the population of interest after a following amplification, of index n+1, in the above-mentioned succession of amplifications; and
$E_n$ is the yield of the amplification reaction of index $\underline{n}$ in the above-mentioned succession of amplifications.

Reformulating this relationship as a recurrence relationship, we obtain:

$$N_{n+1} = (1+E_n)(1+E_{n-1})(1+E_{n-2})\ldots(1+E_0)N_0$$

where $N_0$ is the initial size of the population of interest. So long as the yield $E_n$ is constant, it will be understood that the above relationship can be written more simply as follows:

$$N_{n+1} = N_0 \times (1+E_0)^{n+1}$$

where the index n+1 has not yet reached the changeover region CHO. While the yield is constant during the initial cycles, the following applies:

$$E_n = E_{n-1} = E_{n-2} = \ldots = E_0$$

where $E_0$ is the value of the yield during the constant stage. Nevertheless, when the index n+1 moves into the changeover region CHO, the relationship becomes:

$$N_{n+1} = N_0 \times (1+E_0)^{C_{EEP}} \times \text{function}(C_{EEP}, n+1)$$

where:
($C_{EEP}$−1) is the last index of the amplification reaction during which the yield is still constant (it will thus be understood that the index $C_{EEP}$ itself represents the changeover index proper between the exponential stage and the linear stage); and
the term function ($C_{EEP}$, n+1) is a particular function characterizing the non-constant stage of the yield and that depends at least on the changeover index $C_{EEP}$ and on the current amplification index n+1.

It can thus be seen how it is possible to associate the changeover index $C_{EEP}$ and the initial size $N_0$ of the population of interest. At this stage it can be understood that steps a) and b) of the above-defined method have already been implemented.

A first implementation consists in determining the changeover index $C_{EEP}$ experimentally and in correlating it with the initial size by regression by using a plurality of standard samples that are subjected to the same amplification treatment as the sample of interest. Under such circumstances, it will be understood that steps b) and c) of the above-defined method are merely interchanged since initially the changeover index $C_{EEP}$ (step c)) is determined experimentally, and subsequently the relationship between the index $C_{EEP}$ and the initial size $N_0$ (step b)) is determined in order to end up with the initial size $N_0$ (step d)).

Before describing all of these steps in detail in the meaning of the first implementation, a method is described for determining the index $C_{EEP}$ on the basis of experimental measurements. In particular, it will be understood that this method of determining the index $C_{EEP}$ experimentally can be applied to another implementation that is different from the above-mentioned first implementation.

Returning to the relationship between the effectiveness $E_n$ of a given cycle $\underline{n}$ and the current size of the population of interest in the same cycle $N_n$ and in a subsequent cycle $N_{n+1}$, the effectiveness of the amplification can be expressed as follows:

$$E_n = (N_{n+1}/N_n) - 1$$

In certain circumstances, in particular when there is no need to take account of background noise BN in the measurements, it is possible to a first approximation to assume that the measurements are substantially proportional to the current size of the population of interest. Nevertheless, in practice, account will more often be taken of measurement drift, with corrected experimental measurements $F'_n$ being determined on the basis of direct measurements $F_n$ as shown in FIG. 4A.

A prior step of processing the experimental measurements $F_n$ is preferably applied, this step consisting in subtracting the background noise BN and subsequently in introducing compensation to take account of a non-zero measurement $\epsilon$ representative of the initial population size. In the example shown in FIG. 4A, the variation in the background noise BN as a function of the index $\underline{n}$ can be represented by a linear function since tests have shown that a linear model is satisfactory for fluorescence measurements in PCR. Nevertheless, in certain circumstances it may be preferable to use an exponentially-varying model. In any event, a model is applied that complies best with variation in the background noise BN as given typically by the initial measurement points. Thereafter, the selected model for variation in background noise BN is subtracted from all of the experimental measurement values $F_n$. By applying this step, it will be understood that the theoretical fluorescence measurement $F_0$ is reduced to a measurement value of zero, corresponding to an initial population size $N_0$ of zero, which is not representative of physical reality. Consequently, it is advantageous to apply compensation for this correction as follows:

$$F'_n = F_n - BN + \epsilon$$

where:
the term $F'_n$ corresponds to a corrected measurement for a current index n;
the term $F_n$ corresponds to the raw experimental measurement at said current index n;
the term BN corresponds to the value for the background noise as modeled for the current index n; and
$\epsilon$ is the corresponding compensation term which is assumed to be constant in the example being described and which directly represents the initial population size $N_0$.

Although these steps of correcting for background noise are very advantageous in determining the changeover index $C_{EEP}$, they may also be applied to any determination and quantification of the initial population size $N_0$ whenever background noise is likely to falsify measurement of said population size $N_0$. In this respect, these steps may constitute the subject matter of separate protection, where appropriate.

The corrected measurements $F'_n$ as obtained in this way are advantageously proportional to the current population sizes $N_n$ in the samples of interest, such that the yield $E_n$ can now be expressed directly as a function of measurement values (corrected as described above), by the following relationship:

$$E_n = (F'_{n+1}/F'_n) - 1$$

Thus, from the experimental measurements $F_n$ of FIG. 4A, corrected measurements $F'_n$ are obtained from which there is subsequently determined the variation in the effectiveness $E_n$ as a function of the succession of indices n, as shown in FIG. 4B.

In short, the experimental measurements are expressed in the form of an experimental variation in the effectiveness $E_n$ of the kind shown in FIG. 4B as a function of the succession of amplifications n. This provides an experimentally-determined variation for the yield comprising:
a perceptibly noisy first region for low amplification indices n (specifically prior to the cycle CG in the example of FIG. 4B); and
followed by a second region exhibiting less noise for higher amplification indices (at least after the changeover region CHO).

At least in the most usual circumstance of amplification by PCR and measurement by fluorescence, the non-constant stage of yield is decreasing and corresponds to said second region presenting little noise (as shown in FIG. 4B). Specifically for the purpose of eliminating measurement points that run the risk of falsifying results when selecting a model to apply to the variation in yield:
a crude value $E_0$ is estimated for the constant yield stage; and
particularly when searching for the changeover index $C_{EEP}$, at least some of the measurements in the less noisy second region are ignored for which the estimated yield is less than a threshold value, e.g. corresponding to some fraction of the constant stage $E_0$.

These points NEG (FIG. 4) that are eliminated are typically those that correspond to very high amplification indices n and that might no longer satisfy the model for effectiveness which is selected substantially around the changeover region CHO. By way of example, in order to eliminate them, an average is evaluated for the constant stage of yield $E_0$, typically for the initial indices n. Thereafter, a threshold value is selected that corresponds to a fraction of the average found for the constant stage $E_0$, e.g. 10%. Thereafter, starting from the highest indices n, all measurement points NEG of measured yield lower than or equal to said threshold value are eliminated. This step, which is most advantageous for detecting the index $C_{EEP}$, can nevertheless be applied to any determination based on yield $E_n$, and may constitute the subject matter of separate protection, where appropriate.

When yield presents a non-constant stage in which yield is decreasing and which follows a constant stage, as shown in FIG. 4B, the changeover region CHO is identified by working in the direction of decreasing index numbers n, starting from the less noisy second region, and by detecting a coarse index CG for which the yield passes a predetermined value. Thus, with reference to FIG. 4B, going in the direction of decreasing index numbers n so as to rise towards the changeover region CHO, the yield associated with each index number is evaluated. For the first measurement point of yield that is significantly greater than the above-mentioned predetermined value, it is considered that the above-mentioned coarse index CG has been detected and corresponds to the index of the measurement point.

As described below in a subsequent implementation, it is possible for each measurement point to model the variation in its yield as though said set point itself corresponds to the changeover index $C_{EEP}$. In that implementation, if the constant yield stage $E_0$ is estimated, and if the estimated value exceeds the above-mentioned predetermined value, then the point is considered as corresponding to the coarse index CG.

In general, a maximum yield has a value of 1 so it is possible to select the above-mentioned predetermined value as being equal to 1. Nevertheless, this can be varied, and, for example, provision can be made to set the predetermined value as corresponding to the mean yield $E_0$ as evaluated over the initial reaction cycles.

Thereafter, the estimate of the value of the amplification index $C_{EEP}$ in the changeover region is refined, which value may advantageously be a fraction, by working in the direction of increasing amplification index numbers, starting from the coarse index CG, and by detecting an amplification index for which the yield is approximately equal to the above-mentioned predetermined value. Thus, referring again to FIG. 4B, in order to refine the search for the changeover index $C_{EEP}$ after the coarse index CG has been determined, a search is made downwards starting from the coarse index CG and going in the direction of increasing index number n, in steps of a size smaller than one whole index, and the abscissa value is determined, e.g. by interpolation, at which the predetermined value is crossed. Typically, so long as the constant stage value remains greater than 1, the search is continued in the direction of increasing number n, and the index ($C_{EEP}-1$) preceding the changeover is determined as soon as the constant value $E_0$ is equal to or very close to 1. That is why it is appropriate to select a search step size corresponding to a fraction of the index, for example 10% of one cycle n.

In the above-mentioned first implementation, a plurality of standard samples are provided having respective known initial population sizes, and the succession of amplifications is applied thereto under substantially the same conditions as for the sample of interest. Their respective changeover indices are determined in accordance with above-described steps a), b), and c). In step d):

a dependency relationship is established between the initial population sizes of the standard samples $N_0^{st}$ and their indices $C_{EEP}^{st}$; and after determining the index $C_{EEP}$ for the sample of interest, the initial size of the population of interest $N_0$ is determined by interpolation on that dependency relationship.

Figure 5:
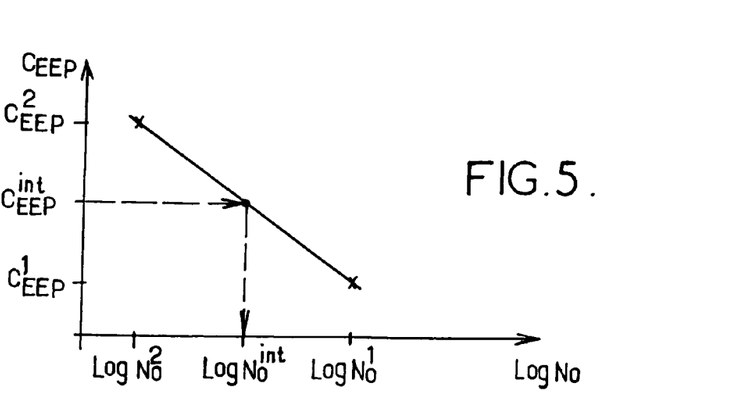
FIG. 5 plots a regression relationship between the yield changeover indices that occur at the changeover between the constant stage and the non-constant stage, and the logarithms of the initial populations for standard samples and for the sample of interest, for use in a first implementation.

Thus, with reference to FIG. 5, a dependency relationship can be established between the changeover cycles $C_{EEP}^1$, $C_{EEP}^2$ of the standards and their initial concentrations $N_0^1$, $N_0^2$ (actually the logarithms thereof), e.g. by regression. By measuring the changeover index $C_{EEP}^{int}$ for the sample of interest and by plotting its value on the regression slope of FIG. 5, the initial concentration $N_0^{int}$ in the sample of interest is obtained by interpolation.

Figure 3:
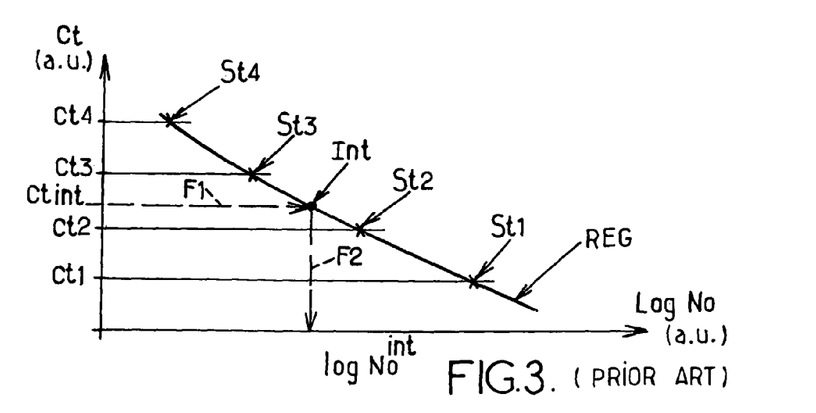
FIG. 3 represents an interpolation method for determining the initial quantity of the population of interest in the sample of interest using a method known in the prior art, and described above.

This first implementation is thus quite similar to that of the prior art described with reference to FIG. 3. Nevertheless, it should not be forgotten that the changeover index $C_{EEP}$ on which this first implementation relies does not correspond in any way to the threshold cycle Ct of the prior art.

In an approach that is significantly different from this first implementation:

in step b), use is made of the yield model to express variation that is parameterized as a function of the succession of amplifications, said variation making use of at least one parameter representing the changeover index $C_{EEP}$; and in step c), at least said parameter representing the changeover index $C_{EEP}$ is determined by comparison with the experimental measurements.

In a second implementation, this parameterized variation is representative of the current population size $N_n$ in the sample of interest.

Typically, this parameterized variation can be drawn from an expression of the type given above:

$$N_{n+1} = N_0 \times (1+E_0)^{C_{EEP}} \times \text{function}(C_{EEP}, n+1)$$

Thus, in addition to a parameter representing the changeover index $C_{EEP}$, this variation makes use of a parameter representative of the initial population size $N_0$ in the sample of interest.

Thereafter, in steps c) and d) of this second implementation, these two parameters $C_{EEP}$ and $N_0$ are determined substantially together.

Previously, in step a), it is necessary to determine a model for the above-mentioned function function($C_{EEP}$, n+1).

Usually, for PCR quantification, a model is selected for the non-constant stage of the yield corresponding to a decreasing exponential having a decrease parameter β which is described in greater detail below. This decrease parameter β is then determined in step c), at least with the changeover index $C_{EEP}$, by comparison with the experimental measurements.

Thus, in this second implementation, once the yield model $E_n$ has been selected, it is applied to the general expression for the current population size $N_n$ given by the above relationship. This provides a model for variation in the current population size $N_n$.

Nevertheless, unless the experimental measurements give the value for the current population size $N_n$ directly (which is rarely true in practice at present), it is appropriate subsequently to model the experimental measurements $F_n$ themselves, taking account of the subtracted background noise and the subsequent compensation ε as described above.

Thus, in a presently preferred implementation, the above-mentioned parameterized variation:

is representative of experimental measurements; and includes a parameter corresponding to a measurement value $F_0$ representative of the initial population size.

Thereafter, the measured value of the initial population size $F_0$ is determined by comparing said parameterized variation $F_n$ with the experimental measurements.

In order to perform this comparison, it is possible, for example, to adjust the parameters $F_0$, $E_0$, $C_{EEP}$ and the decrease parameter β in the model of the measurements $F_n$ by using statistical correlations (typically the least squares method) applied to the raw experimental measurements. An example implementation is described in detail below.

Figure 6A:
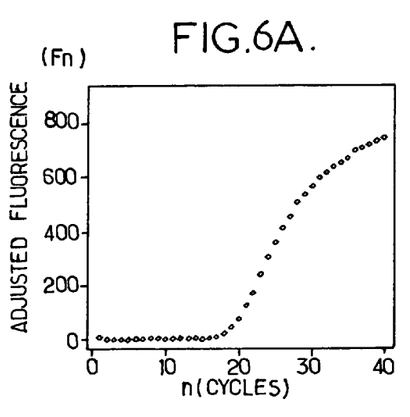
FIG. 6A shows typical variation in the measured quantity of fluorescence after it has been adjusted by taking account of background noise specific to the measurements, and plotted as a function of the number n of PCR reaction cycles.

Initially, variation is obtained for the measured and adjusted quantity of fluorescence as a function of the number of PCR cycles that have been applied, as shown for example in FIG. 6A. This figure shows the amplification curve for a sample of interest containing nucleic acids, in this case a fragment of DNA having an initial quantity of 100,000 copies, marked by the SYBRGREEN intercalant during the PCR reaction which is performed on the 1-CYCLER IQ apparatus from the supplier BI-RAD®.

In the example described, it will be understood that the amplification reaction is a PCR reaction in real time. The experimental measurement represents quantities of emitted fluorescence.

The fluorescence of cycle $\underline{n}$ after adjustment for background noise, as described above, is written $F_n$ below. The theoretical initial fluorescence before the first cycle is written $F_0$. The effectiveness of the PCR in cycle $\underline{n}$ is written $E_n$. The total number of cycles performed during the PCR reaction is written N.

By assumption, the fluorescence measured on each cycle $\underline{n}$ of the PCR reaction cycle is defined by:

$$F_{n+1} \approx F_n(1+E_n) \text{ for all } n \in \{0, 1, 2, \ldots, N-1\} \quad (1)$$

with $0 \leq E_n \leq 1$.

The effectiveness of the reaction on each cycle $\underline{n}$ is calculated as follows:

$$E_n = \frac{N_{n+1}}{N_n} - 1 \approx \frac{F_{n+1}}{F_n} - 1 \text{ for all } n \in \{0, 1, 2, \ldots, N-1\} \quad (2)$$

It should be observed that equation (1) is assumed to be true for n=0. Nevertheless, by definition, the initial fluorescence $F_0$ is unknown. It is therefore not possible to calculate the effectiveness on the first cycle $E_0$ directly for formula (2).

Figure 6B:
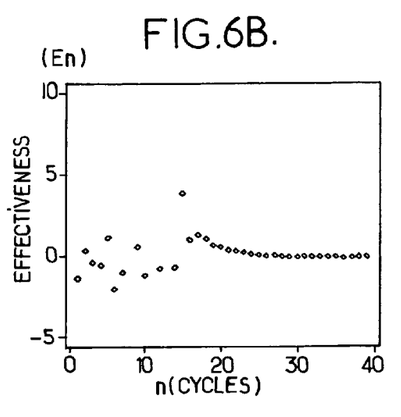
FIG. 6B shows the variation in the effectiveness of the PCR shown in FIG. 6A as a function of the number $\underline{n}$ of cycles.

FIG. 6B shows the effectiveness of the PCR reaction as approximated by formula (2) and on the basis of the adjusted variation in fluorescence of FIG. 6A, as a function of cycle number $\underline{n}$.

The following assumptions are preferably made:

the effectiveness of the reaction is relatively constant during the initial cycles; and after a certain number of cycles have been performed, the effectiveness of the reaction decreases.

FIG. 6B confirms the second assumption since it can be seen that effectiveness decreases as from cycle n=17. However, the measured effectivenesses in cycles 1 to 16 are very noisy, which makes it difficult to verify the first assumption graphically.

Nevertheless, it is preferable to assume that variation in effectiveness obeys a model of the type including:
- a first stage that is constant between the first PCR cycle and the cycle ($C_{EEP}-1$) preceding the changeover cycle written $C_{EEP}$; and
- a second stage in which it decreases for cycles of numbers greater than or equal to cycle ($C_{EEP}-1$).

The cycle ($C_{EEP}-1$) thus represents the last cycle (which may be a fraction) for which effectiveness continues to be constant.

It is then proposed to model the effectiveness of the reaction as follows:

$$E_n = \begin{cases} E_0 & \text{for } 0 \leq n \leq (C_{EEP} - 1) \\ (1 + E_0)^{exp(-\beta(n-C_{EEP}+1))} - 1 & \text{for } (C_{EEP} - 1) \leq n \leq (N - 1) \end{cases} \quad (3)$$

where $E_0$ and $\beta$ are real parameters which are estimated using the amplification curve of FIG. 6A, or using the effectiveness curve of FIG. 6B in a manner described below.

In a variant, some other selection may be preferred, e.g. from the models F1 to F3 given below, particularly depending on the type of nucleic acid that is to be quantified.

$$E_n = \exp(-\beta(n-C_{EEP}+1))-1 \quad F1$$

$$E_n = \exp(-\mu(n-C_{EEP}+1))^\alpha)-1 \quad F2$$

$$E_n = \alpha \cdot \exp(-\mu(n-C_{EEP}+1)^\alpha)-1 \quad F3$$

Preferably, several sets of parameters are estimated in step c) for several candidate changeover cycles $C_{EEP}$, and the minimum candidate cycle is selected for which the associated parameters maximize the statistical correlations that can be undertaken in step c), for each changeover cycle $C_{EEP}$.

As mentioned above, expression (1) may also be written in the form:

$$F_n = F_0 \prod_{k=0}^{n-1}(1 + E_k) \text{ for } n \in \{1, 2, \ldots, N\} \quad (4)$$

Thus, by introducing the expression (3) for effectiveness into formula (4), a new model is obtained having four parameters ($F_0$, $E_0$, $\beta$, $C_{EEP}$) for the adjusted emitted fluorescence $F_n$:

$$F_n = \begin{cases} F_0(1 + E_0)^n & \text{for } 1 \leq n \leq C_{EEP} \\ F_0(1 = E_0)^{C_{EEP}+\frac{1-exp(-\beta(n-C_{EEP}))}{exp(\beta)-1}} & \text{for } C_{EEP} \leq n \leq N \end{cases} \quad (5)$$

The initial size $N_0$ of the population of interest, the effectiveness $E_0$ of the reaction of $n=0$, the parameter $\beta$, and the changeover cycle $C_{EEP}$ are evaluated repetitively for several cycle values in the vicinity of the changeover region CHO in order to find a statistical correlation maximum that is achieved for a minimum cycle value that is equal to the changeover cycle $C_{EEP}$.

In this second implementation, it is preferred to model variation in the measured and adjusted quantities of fluorescence as a function of cycle number on the basis of the models or variation in effectiveness, and subsequently to carry out the correlations directly on the measured and adjusted quantities of fluorescence.

It should be observed that by adjusting the measured emitted fluorescence for background noise, an artificial adjustment is also made on the initial fluorescence $F_0$. Thus, estimating the parameters of the effectiveness model on the basis of effectiveness measurements that are deduced from adjusted fluorescence measurements constitutes an additional source of error and it might be preferable to proceed in two stages as described below for the third implementation.

Nevertheless, the second implementation as described is simpler and adapts well to PCR quantification using fluorescence measurements. It is based on the real measurements of fluorescence $F'_n$ which correspond to the fluorescence measurements adjusted for drift in background noise together with compensation $\epsilon$ on said measurements. Once the background noise has been subtracted, we have a relationship of the following type:

$$F'_n = F_n + \epsilon$$

where $\epsilon$ is a quantity that may or may not depend on cycle number $\underline{n}$. It is preferably selected to be constant.

Under such circumstances, the measured and "adjusted" effectiveness also written $E'_n$ on cycle $\underline{n}$ is defined by:

$$E'_n = \frac{F'_{n+1}}{F'_n} - 1 = \frac{F_{n+1}+\varepsilon}{F_n+\varepsilon} - 1 \text{ for all } n \in \{1, 2, \ldots, N-1\} \quad (7)$$

The model of above relationship (5) thus becomes:

$$F_n = \begin{cases} F'_0(1 + E'_0)^n & \text{for } 1 \leq n \leq C_{EEP} \\ F'_0(1 + E'_0)^{C_{EEP}+\frac{1-exp(-\beta'(n-C_{EEP}))}{exp(\beta')-1}} & \text{for } C_{EEP} \leq n \leq N \end{cases} \quad (8)$$

Under such circumstances, the effectiveness values $E'_n$ are approximated experimentally from the measurements so as to be able to set a minimum acceptable effectiveness threshold during the stage of decreasing effectiveness. A threshold cycle is thus determined beyond which the adjusted fluorescence measurements are not used for the purposes of the model (points NEG in FIG. 4B). Typically, the threshold cycle corresponds to the first cycle in the stage of decreasing effectiveness at which effectiveness drops below some minimum acceptable effectiveness threshold (e.g. $0.1E_0$).

More generally, the value of the effectiveness threshold preferably lies in the range 0 to 0.5, and PCR having an effectiveness value below said threshold is potentially biased by uncontrolled inhibition phenomena.

Figure 7:
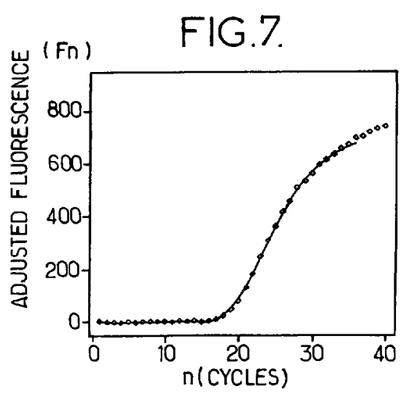
FIG. 7 compares the experimental variation in emitted fluorescence as shown in FIG. 6A with the results obtained by applying the emitted fluorescence model obtained by including an effectiveness model in a second implementation.
Figure 8:
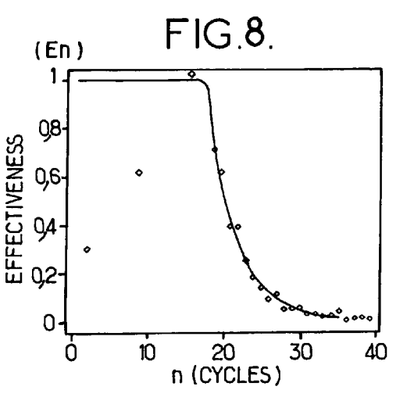
FIG. 8 is a comparison between the variation in the effectiveness of FIG. 6B and the application of an effectiveness model deduced from the emitted fluorescence model of FIG. 7.

In the example shown in FIG. 7, the threshold value for effectiveness was set at 0.02 (i.e. 2% of $E_0$) The threshold cycle $C_s$ corresponded to cycle $n=36$. FIG. 7 shows the adjusted measurements of emitted fluorescence. It can be seen that there is satisfactory correlation with the model (continuous line) for those experimental measurements (marked with an "o") up to cycle $n=36$. FIG. 8 also shows good correlation with experimental measurements for predictive effectiveness as obtained from FIG. 7 using the model based on measured and adjusted fluorescence.

The main steps of this implementation can be summarized as follows, with reference to FIG. 9.

In a start step 70, the measured values for quantities of fluorescence have been obtained and adjusted relative to background noise as a function of cycle number $\underline{n}$, as shown in FIG. 6A.

In step 71, an approximation for effectiveness of the reaction in cycle n is calculated using above formula (2) for each of the cycles n=1, 2, ..., (N−1).

In step 72, the minimum cycle $C_s$ is determined for which the following two conditions are satisfied:
- the cycle $C_s$ lies in the stage of decreasing effectiveness; and
- the effectiveness of the threshold cycle is less than the threshold effectiveness value $E_s$ (e.g. $E_s=0.1E_0$):

$$E_{C_s} \leq E_s$$

It is already possible to eliminate the points NEG for which effectiveness is less than $E_s$.

In step 73, a model is formed for the curve of adjusted emitted fluorescence which effectiveness is decreasing over the cycle range $C_{EEP}=(C_s-5)$ to $C_s$, using expression (8) in which it is assumed that compensation $\epsilon$ is given by $\epsilon=F'_0$:

$$F_n = F'_0(1+E'_0)^{C_{EEP}+\frac{1-exp(-\beta'(n-C_{EEP}))}{exp(\beta')-1}} - F'_0$$

Thereafter, test 74 on the value $\hat{E}'_0$ estimated for the value $E'_0$ and the decrementation in step 75 of the value for the changeover cycle $C_{EEP}$ seeks to find the looked-for value of $C_{EEP}$ using a step size P (which may be equal to 1), and in repeating step 73 so long as the value of $\hat{E}'_0$ is less than 1.

Thereafter, when the estimated effectiveness value exceeds the value 1 (arrow n on exiting the test 74), the value of the index $C_{EEP}$ is incremented by a step of size h (which may be a fraction smaller than unity) in step 76 and in step 77 fluorescence $F_n$ is modeled in the same manner as in step 73. So long as the estimated effectiveness $\hat{E}'_0$ is greater than or equal to 1 in step 78, steps 76 to 78 are repeated. When the estimated effectiveness takes a value of less than 1, the estimated parameters ($\hat{F}'_0, \hat{E}'_0, \hat{\beta}'_0, \hat{C}_{EEP}$) are conserved in an end step 79.

In this step, a value $\hat{F}'_0$ has finally been obtained that alone is representative of the initial population size $N_0$ in the sample of interest. It is then possible to use at least one standard sample having a known population size $N_0^{st}$ so as to determine in step 80 the initial population size $N_0$ in the sample of interest.

For this purpose, a measured value of an initial population size $F_{0st}$ in a standard sample of known initial population $N_{0st}$ is obtained. Thereafter, the value of the initial population size $N_0$ in the sample of interest is obtained by deriving a proportionality relationship between the measurement for the standard sample and its known initial population size, and applying that relationship to the measurement $F'_0$ to obtain the actual initial population size $N_0$.

Figure 9:
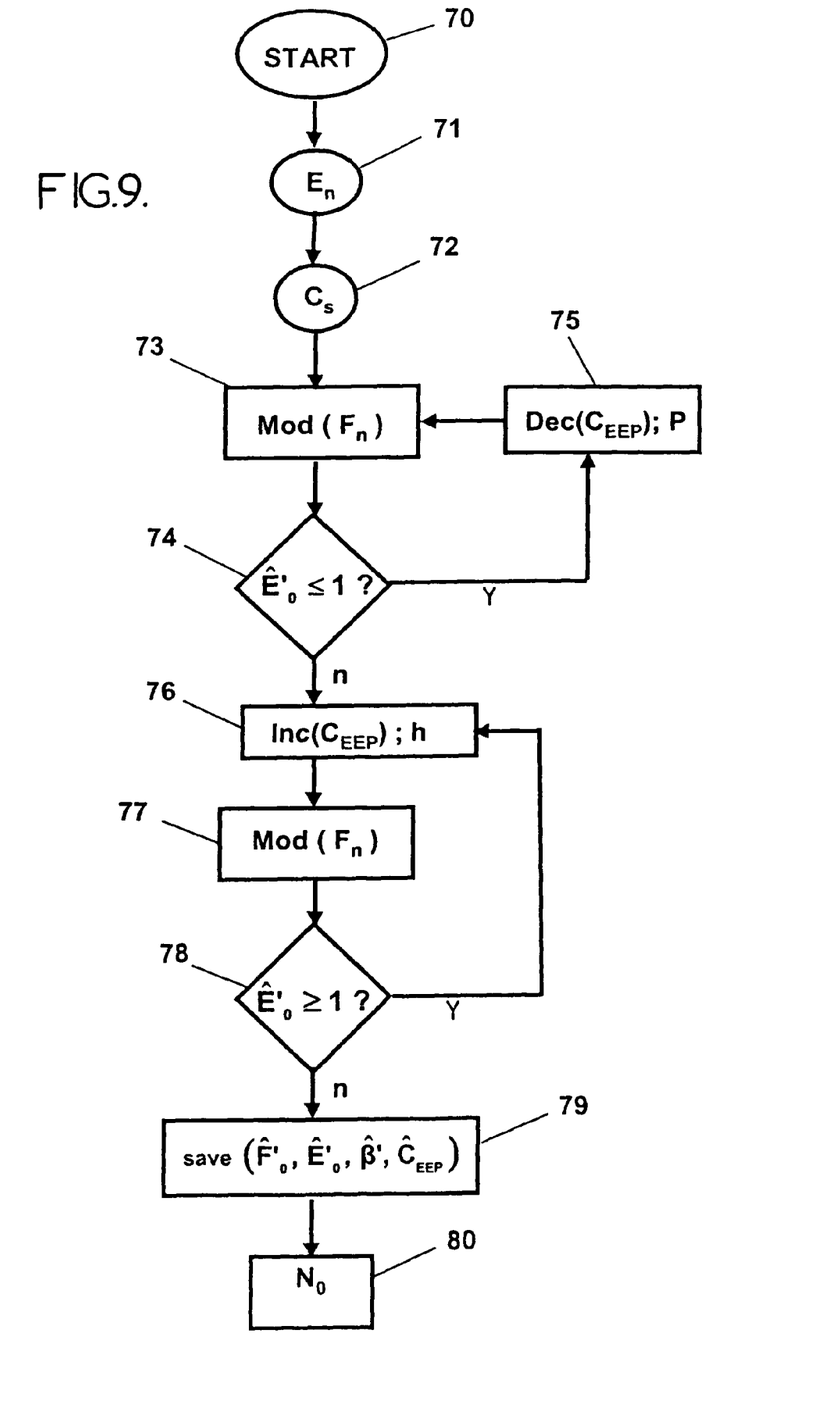
FIG. 9 is a flow chart outlining the main steps in the method in a proposed implementation of the present invention.

In other words, in step 80 of FIG. 9, it is possible to determine the value $N_0$ of the initial population size in the sample of interest by applying a simple proportionality relationship of the type:

$$N_0 = \hat{F}'_0(N_{0st}/\hat{F}'_{0st})$$

implying that the initial population size in the standard $N_{0st}$ and the ratio of the corrected fluorescences as compensated and estimated by adjusting the fluorescence model apply both to the sample of interest and to the standard sample.

It will thus be understood that a single standard ought to be sufficient for determining the initial size of the population of interest in the sample of interest, which is an advantage provided by the invention.

Nevertheless, in a variant, and where necessary, provision could also be made to obtain respective measured values for initial population sizes $\hat{F}'_{0st}$ in a plurality of standard samples having known initial population sizes $N_{0st}$. Thereafter, a dependency relationship is established between the initial population sizes $N_{0st}$ of the standard samples and the respective measured values for their initial population sizes $\hat{F}'_{0st}$. Thereafter, after finding the measured value for the initial population size of the sample of interest $\hat{F}'_0$, the actual initial population size $N_0$ of interest is determined by interpolation using the dependency relationship. It will be understood that this dependency relationship may also typically be a regression of the type shown in FIG. 5, but having the initial fluorescence values $\hat{F}'_{0st}$ and $\hat{F}'_0$ of the standards and of the sample of interest plotted up the ordinate (or the values of their respective logarithms) instead of plotting values for the changeover index $C_{EEP}$.

Once use is made of one or more standards, provision can be made for one or more standard samples having respective known initial population sizes $N_{0st}$ to which the succession of amplification reactions is applied under substantially the same conditions as for the sample of interest. Thereafter, the measured values $\hat{F}'_{0st}$ for their initial population sizes are determined by making comparisons of the parameterized variations with the experimental measurements, as for the sample of interest.

In other words, the same calculations are naturally applied concerning the measured and adjusted quantities of fluorescence both on the standard(s) and on the sample of interest. The quantity of fluorescence $\hat{F}'_{0st}$ before the first cycle is estimated for the standard(s) using the same method as is used for determining $\hat{F}'_0$ for the sample of interest, as described above.

A third implementation, corresponding to a variant of the above-described second implementation consists overall in adjusting the model for the effectiveness $E_n$ relative to the experimental measurements, and in subsequently injecting said adjusted effectiveness model into the model for the current population size $N_n$, or into the model for the measurement $F_n$. This third implementation can be summarized as follows.

The parameterized variation constructed in step b) is representative of yield, and in step c), experimental variation of the yield is determined on the basis of experimental measurements in order to compare the parameterized variations with the experimental variation. Thereafter, in order to obtain a parameter representative of the initial population size $N_0$ the following steps are performed in step d):

d1) determining a second parameterized variation representative of the current population size $N_n$ in the sample of interest, making use at least of the parameter representing the changeover index $C_{EEP}$, and a parameter representative of the initial population size $N_0$;

d2) applying to said second variation, a parameterized value for the changeover index $C_{EEP}$ as determined in step c); and d3) adjusting at least the parameter representative of the initial population size $N_0$ by direct comparison of the second variation with the experimental measurements.

Advantageously the following are performed:
  in step d2), applying a coarse value for the changeover index $C_{EEP}$ in the same manner as described for detecting it with reference to above FIG. 4B; and
  in step d3), subsequently refining the index value together with adjusting the parameter representative of the initial population size $N_0$.

Finally, it should be understood that the presently preferred second implementation of FIGS. 7 and 8 differs from this third implementation by the fact that no attempt is made to perform correlations on effectiveness, but use is made merely of the mathematical model for effectiveness variation in order to model and refine the estimate of the correct and compensated fluorescence.

Naturally, the present invention is not limited to the embodiments described above by way of example, and it extends to other variants.

Thus, it will be understood that the present invention can also apply to relative quantification, in particular by PCR. In this application, as well as amplifying the population of interest, a reference population is also amplified either simultaneously in the same medium, or separately. Measurements are taken as follows:

experimental measurements representative of the size of the population of interest; and experimental measurements representative of the reference population size.

The method can then continue by applying steps a), b), and c) to the reference population while step d) consists merely in determining a ratio between the respective initial sizes of the population of interest and of the reference population.

Relative quantification can be used for analyzing the expression of a gene of interest during the development of an organism. In order to correct in particular for variations in quantity and in quality between samples taken from the organism at different times, in addition to analyzing the target gene of interest, a reference gene is also analyzed that is known for having a level of expression that remains stable during development.

A final step then consists in comparing the ratios $$\frac{N_{0target}}{N_{0ref}}$$

between the various samples that have been taken.

In order to achieve the desired results, two strategies are possible.

The prior art strategy is based on detecting the threshold cycle Ct and it normally takes place as follows. For each sample taken at different instants t0, t1, t2, ..., tn, the ratio $$\frac{N_{0target}}{N_{0ref}}$$

is determined, making use of at least one standard (i.e. a standard for which $N_{0target}$ and $N_{0ref}$ are known), which amounts to performing two successive absolute quantifications followed by calculating a ratio.

Another strategy that is particularly advantageous in the context of the invention consists in determining for each sample taken at different instants t0, t1, t2, ..., tn the ratio:

$$\frac{\left(\frac{N_{0target}}{N_{0ref}}\right)_{sample}}{\left(\frac{N_{0target}}{N_{0ref}}\right)_{sample\_t0}}$$

directly by using the following formula:

$$\frac{\left(\frac{N_{0target}}{N_{0ref}}\right)_{sample}}{\left(\frac{N_{0target}}{N_{0ref}}\right)_{sample\_t0}} = \frac{\frac{(F_{0target})_{sample}}{(F_{0target})_{sample\_t0}}}{\frac{(F_{0ref})_{sample}}{(F_{0ref})_{sample\_t0}}}$$

In this second implementation, which in the end makes use only of the parameter $F_0$, in combination with the technique of the invention, no standard sample is needed, which is particularly advantageous.

Figure 10:
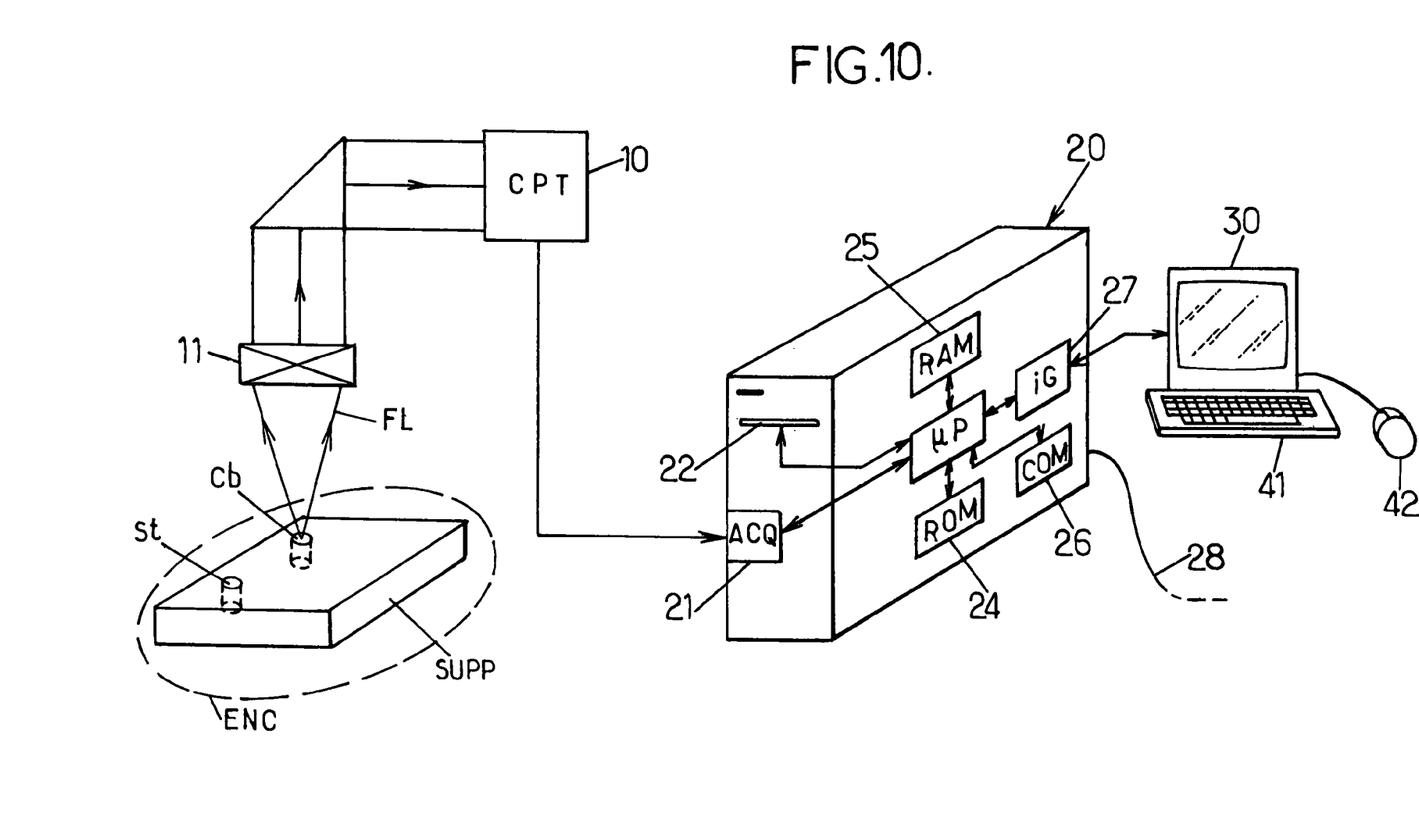
FIG. 10 is a diagram of an installation for quantifying the initial population of a sample of interest.

Reference is now made to FIG. 10 which shows an installation for implementing the method of the invention. It comprises a support SUPP in this case comprising a well containing the sample of interest ECH and a well containing a standard sample referenced St, for example. The support SUPP is enclosed in an enclosure ENC, e.g. fitted with heater means (not shown) for applying a PCR reaction to the standard and to the sample of interest.

In the example described, provision is preferably made to take measurements of the quantities of fluorescence emitted on each cycle, both by the standard St and by the sample of interest ECH. To this end, a selected reagent is inserted into the wells and the samples are illuminated by a lamp (e.g. a halogen-tungsten lamp) in order to measure the respective quantities of fluorescence coming from the sample of interest and from the standard sample on each PCR cycle that is applied. In addition, an apparatus for detecting fluorescence comprises, for example, an objective lens 11 for collecting the light coming from the fluorescence, and photon counting means 10, e.g. a charge-coupled device (CCD) camera, and/or photomultipliers, in order to measure the fluorescence emitted on each PCR cycle from the sample of interest and from the standard. Thus, the fluorescence emitted by each well is advantageously focused by the lens 11 and then is preferably detected by a CCD camera 10 connected to an acquisition card 21, e.g. of the Personal Computer Memory Card International Association (PCMCIA) type provided in a central unit 20 of a computer.

The computer is then connected to the above-mentioned measuring means 10 to receive therefrom signals that are representative of the measured quantities of fluorescence detected on each PCR cycle, and to process these signals in order to determine an initial size for the population of interest prior to the first cycle, by implementing the method of the invention.

Typically, the processor unit comprises the following:

an acquisition card 21 connected to the measurement means 10;

working memory 25 (e.g. of the random access memory (RAM) type) for temporary storage and processing of the above-mentioned signals;

permanent memory 24 for storing the computer program product in the meaning of the invention and for storing the data that has been processed and that is ready for use, e.g. in subsequent diagnosis;

where appropriate, a reader 22 of a memory medium such as a CD-ROM, for example, which may initially carry the computer program product;

optionally a communications interface 26 for communicating with a local or remote site (connection 28), e.g. for transmitting the processed data so as to enable a diagnosis to be made remotely concerning a patient;

a graphics interface 27 typically connected to a display screen 30; and a processor 23 for managing the interactions between these various items of equipment.

The computer may also have input members such as a keyboard 41 and/or a mouse 42 connected to the central unit 20.

Nevertheless, it should be understood that in the meaning of the invention the installation comprises overall:

a sample support SUPP, at least for the sample of interest;

a first apparatus ENC for applying said succession of amplification reactions at least to the population of interest in the sample of interest;

a second apparatus 10 for taking measurements representative of the current size of the population of interest; and computer means 20 suitable for receiving measurement signals from the second apparatus 10 and for implementing all or some of the steps of the method of the invention.

For this purpose, a computer program product can be used for controlling the computer means. The program may be stored in a memory of the processor unit 20 or on a removable memory medium (CD-ROM etc.) and suitable for co-operating with the reader of the processor unit. The computer program in the meaning of the invention then contains instructions for implementing all or some of the steps of the method of the invention. For example, the algorithm of the program may be represented by a flow chart equivalent to the diagram of FIG. 9.

The invention claimed is:

1. A method to quantify an initial population of nucleic acids in a sample of interest subjected to a population amplification reaction comprising a succession of repeated amplification cycles, the method comprising performing by means of an apparatus experimental measurements representative of a current size of the population of the sample of interest during the repeated amplification cycles and further comprising the following steps:

a) providing a model of the yield of the amplification reaction, this model corresponding to the variation of the yield in function of the number of amplification cycles and being represented by a curve having:

a first constant portion corresponding to a first part of the succession of repeated amplification cycles;

a second non-constant portion corresponding to a second part of the succession of repeated amplification cycles;

and a changeover region uniting the first and second portions of the curve, said region having a changeover index C equal to a corresponding number of amplification cycles;

b) determining a relationship between the changeover index $C_{EEP}$ and a parameter No representative of the initial population size in the sample of interest from the following formula:

$$N_{n+1} = N_0 \times (1+E_0)^{C_{EEP}} \times \text{function}(C_{EEP}, n+1)$$

where $N_{n+1}$ is a parameter representative of the population size at the current amplification index, $E_0$ is the value of the yield at the first constant portion of the yield model, the term function ($C_{EEP}$, n+1) is a particular function characterizing the second non-constant portion of the yield model and that depends at least on the changeover index $C_{EEP}$ and on the current amplification index n+1, and ($C_{EEP}$−1) is the last index of the amplification reaction during which the yield is still constant; and c) determining an experimental variation of the yield and a changeover index value from the experimental measurements performed by said apparatus during the repeated amplification cycles, and d) determining the initial population size in the sample of interest from the changeover index value by means of the relationship between the changeover index and the said parameter representative of the initial population size.

2. A method according to claim 1, including in step b), using the yield model to determine a variation of the current population size in function of the number of repeated amplification cycles, of the changeover index and of the initial population size, and in steps c) and d), determining the values of the changeover index and of the initial population size.

3. A method according to claim 2, including providing a plurality of standard samples having respective known initial population sizes, applying said succession of repeated amplification cycles to the standard samples under the same conditions as for the sample of interest, and determining their respective changeover indices in application of steps a), b), and c), and, in step d):

establishing a dependency relationship between the initial population sizes of the standard samples and their changeover indices; and after determining the changeover index for the sample of interest, determining the initial size of the population of interest by interpolation on said dependency relationship.

4. A method according to claim 1, including in step b), using the yield model to determine a parameterized variation of the yield in function of the changeover index, of the number of repeated amplification cycles and of the initial population size, and in step c), comparing the experimental variation of the yield with the parameterized variation of the yield.

5. A method according to claim 4, including, in step d):

d1) determining a parameterized variation of the current population size in the sample of interest, in function of the changeover index and of the initial population size in the sample of interest;

d2) applying the changeover index value as determined in step c) to the parameterized variation of the current-population size, and d3) adjusting the value of the initial population size by direct comparison of the parameterized variation of the current population size with the experimental measurements.

6. A method according to claim 5, including:

in step d2), applying a coarse value of the changeover index to the said parameterized variation of the current population size, in step d3), refining the value of the changeover index while adjusting the value of the initial population size.

7. A method according to claim 6, wherein said parameterized variation of the current population size:

is representative of said experimental measurements; and includes a parameter corresponding to a measured value representative of the initial population size, and wherein the measured value of the initial population size is determined by comparing said parameterized variations with the experimental measurements.

8. A method according to claim 1, including applying a prior step of processing the experimental measurements, which step comprises subtracting a background noise from the measurements and introducing a compensation value corresponding to the initial population size.

9. A method according to claim 8, including obtaining a measurement value for an initial population size in a standard sample having a known initial population size and deriving a proportionality relationship between the measurement value and the known initial population size; and determining the value of the initial population size in the sample of interest by applying the same proportionality relationship between the initial population size and its measurement to the sample of interest.

10. A method according to claim 9 including providing at least one standard sample having respective known initial population size, applying the succession of repeated amplification cycles to said standard sample under the same conditions as for the sample of interest, and determining the measured value of its initial population size by comparing the parameterized variations of its current population size with the experimental values.

11. A method according to claim 8, including obtaining respective measurement values for the initial population sizes in standard samples having known initial population sizes, and:
establishing a dependency relationship between the initial population sizes of the standard samples and the corresponding measurement values for their respective initial population sizes; and
after determining the measured value for the initial population size of the sample of interest, determining the initial size of the population of interest by interpolation on said dependency relationship.

12. A method according to claim 1, including:
expressing the experimental measurements in the form of an experimental variation of yield as a function of the number of repeated amplifications cycles
said experimental variation of yield comprising:
a first region that is substantially subject to noise for low numbers of repeated amplification cycles; and
followed by a second region with less noise for higher numbers of repeated amplification cycles.

13. A method according to claim 12, in which said second portion of the yield is one of decreasing yield, the method including:
estimating a coarse value for the first portion of yield; and
at least when seeking the changeover index, ignoring at least some of the measurements in said less noisy second region for which the estimated yield is below a threshold value.

14. A method according to claim 12, in which said second portion of the yield is a stage of decreasing yield, the method including identifying said changeover region by working in the direction of decreasing numbers of repeated amplification cycles starting from said second region, and detecting a coarse value of the changeover index at which the yield exceeds a predetermined value.

15. A method according to claim 14, wherein the detected coarse value of said changeover index is refined by working in the direction of increasing numbers of repeated amplification cycles starting from the coarse value, by detecting a changeover index for which the yield is approximately equal to said predetermined value.

16. A method according to claim 1, including modeling said second portion of the yield by a decreasing exponential including a decrease parameter, and determining said decrease parameter in step c) with the changeover index by comparison with the experimental measurements.

17. A method according to claim 1, in which the amplification reaction is a polymerase chain reaction performed in real time.

18. A method according to claim 1, in which said experimental measurements are measured quantities of emitted fluorescence.

19. A method to quantify an initial population of nucleic acids of interest relative to an initial population of reference nucleic acids, said initial population of nucleic acids of interest and said initial population of reference nucleic acids being subjected to a population amplification reactions comprising a succession of repeated amplification cycles, the method comprising performing by means of an apparatus experimental measurements representative of a current size of the population of interest and experimental measurements representative of a current size of the reference population during the repeated amplification cycles and further comprising the following steps: for said population of interest:

a) providing a model of the yield of the amplification reaction, this model corresponding to the variation of the yield in function of the number of amplification cycles and being represented by a curve having:
a first constant portion corresponding to a first part of the succession of repeated amplification cycles;
a second non-constant portion corresponding to a second part of the succession of repeated amplification cycles;
and a changeover region uniting the first and second portions of the curve, said region having a changeover index CEEP equal to a corresponding number of amplification cycles;

b) determining a relationship between the changeover index CEEP and a parameter No representative of the initial population size in the population of interest from the following formula:

$$N_{n+1} = No \times (1+Eo)^{c_{EEP}} \times \text{function}(C_{EEP}, n+1)$$

where $N_{n+1}$ is a parameter representative of the population size at the current amplification index, E0 is the value of the yield at the first constant portion of the yield model, the term function (CEEP, n+1) is a particular function characterizing the second non-constant portion of the yield model and that depends at least on the changeover index CEEP and on the current amplification index n+1, and (CEEP−1) is the last index of the amplification reaction during which the yield is still constant; and c) determining an experimental variation of the yield and a changeover index value from the experimental measurements performed by said apparatus during the repeated amplification cycles, and d) determining the initial population size in the population of interest from the changeover index value by means of the relationship between the changeover index and the said parameter representative of the initial population size; and for said reference population:

1) providing a model of the yield of the amplification reaction, this model corresponding to the variation of the yield in function of the number of amplification cycles and being represented by a curve having:
a first constant portion corresponding to a first part of the succession of repeated amplification cycles;
a second non-constant portion corresponding to a second part of the succession of repeated amplification cycles;
and a changeover region uniting the first and second portions of the curve, said region having a changeover index CEEP equal to a corresponding number of amplification cycles;

2) determining a relationship between the changeover index CEEP and a parameter No representative of the initial population size in the reference population from the following formula:

$$Nn+1 = N0 \times (1+E0)^{CEEP} \times \text{function}(CEEP, n+1)$$

where Nn+1 is a parameter representative of the population size at the current amplification index, E0 is the value of the yield at the first constant portion of the yield model, the term function (CEEP, n+1) is a particular function characterizing the second non-constant portion of the yield model and that depends at least on the changeover index CEEP and on the current amplification index n+1, and (CEEP−1) is the last index of the amplification reaction during which the yield is still constant;

3) determining an experimental variation of the yield and a changeover index value from the experimental measurements performed by said apparatus during the repeated amplification cycles;

4) determining the initial population size in the reference population from the changeover index value by means of the relationship between the changeover index and the said parameter representative of the initial population size; and 5) determining a ratio between the initial population size in the population of interest determined at step d) and the initial population size in the reference population determined at step 4).

20. An installation comprising:
a sample support for supporting at least a sample of interest;
a first apparatus for applying a succession of repeated amplification cycles to a population of interest in the sample of interest;
a second apparatus for performing experimental measurements representative of a current size of the population of interest; and
computer means suitable for receiving measurement signals from the second apparatus and implementing the following steps:
on the basis of a model of the yield of the amplification cycles as a function of the of amplification cycles, said model comprising
a first constant portion for a first part of the succession of amplification cycles, and
a second non-constant portion for a second part of the succession of amplification cycles,
the first and second portions being united by a changeover region in which yield changes over between the constant and non-constant portions, said region having a changeover index equal to a corresponding number of amplification cycles;
using said yield model to determine a relationship between the changeover index $C_{EEP}$ and a parameter $N_0$ representative of the initial population size in the sample of interest from the following formula:

$$N_{n+1} = N_0 \times (1+E_0)^{C_{EEP}} \times \text{function}(C_{EEP}, n+1)$$

where $N_{n+1}$ is a parameter representative of the population size at the current amplification index, $E_0$ is the value of the yield at the first constant portion of the yield model, the term function ($C_{EEP}$, n+1) is a particular function characterizing the second non-constant portion of the yield model and that depends at least on the changeover index $C_{EEP}$ and on the current amplification index n+1, and ($C_{EEP}$−1) is the last index of the amplification reaction during which the yield is still constant;
determining a variation of the yield and a changeover index value from the experimental measurements; and,
determining the initial population size in the sample of interest from the changeover index value by means of the said relationship.

21. A computer program product stored in a memory of a processor unit or on a removable memory medium suitable for co-operating with a reader of said processor unit, wherein said program product comprises instructions for implementing a method implemented by computer means to quantify an initial population of nucleic acids in a sample of interest subjected to a succession of repeated amplification cycles, during which experimental measurements are taken representative of a current size of the population of at least the sample of interest, the method comprising the following steps:
a) providing a model of the variation of the yield of the amplification cycles as a function of the number of repeated amplification cycles, said model comprising:
a first constant portion for a first part of the succession of amplification cycles; and
a second non-constant portion for a second part of the succession of amplification cycles;
the first and second portions being united by a changeover region in which yield changes over between the constant and non-constant portions, said region having a changeover index equal to a corresponding number of repeated amplification cycles;
b) using the yield model to determine a relationship between the changeover index $C_{EEP}$ and a parameter $N_0$ representative of the initial population size in the sample of interest from the following formula:

$$N_{n+1} = N_0 \times (1+E_0)^{C_{EEP}} \times \text{function}(C_{EEP}, n+1)$$

where $N_{n+1}$ is a parameter representative of the population size at the current amplification index, $E_0$ is the value of the yield at the first constant portion of the yield model, the term function ($C_{EEP}$, n+1) is a particular function characterizing the second non-constant portion of the yield model and that depends at least on the changeover index $C_{EEP}$ and on the current amplification index n+1, and ($C_{EEP}$−1) is the last index of the amplification reaction during which the yield is still constant;
c) determining a variation of the yield and a changeover index value from the experimental measurements; and
d) determining the initial population size in the sample of interest from the changeover index value by means of the said relationship.

* * * * *